United States Patent [19]

Boron

[11] Patent Number: 4,487,082
[45] Date of Patent: Dec. 11, 1984

[54] MOLTEN METAL SAMPLER FOR JOMINEY TEST

[75] Inventor: Joseph J. Boron, Medina, Ohio

[73] Assignee: Midwest Instrument Co., Inc., Hartland, Wis.

[21] Appl. No.: 453,010

[22] Filed: Dec. 27, 1982

[51] Int. Cl.³ .............................................. G01N 1/12
[52] U.S. Cl. ............................ 73/864.55; 73/864.53; 249/97
[58] Field of Search ........... 73/864.55, 864.53, 864.56, 73/DIG. 9; 249/DIG. 4, 97, 96, 85

[56] References Cited

U.S. PATENT DOCUMENTS

| | | | |
|---|---|---|---|
| 3,559,452 | 2/1971 | Perbix et al. | 73/864.55 X |
| 3,774,453 | 11/1973 | Falk | 73/864.55 |
| 3,859,857 | 1/1975 | Falk | 73/DIG. 9 |
| 3,897,689 | 8/1975 | Boron | 73/864.56 |
| 3,994,172 | 11/1976 | Kelsey | 249/DIG. 4 |
| 4,004,773 | 1/1977 | Binder | 249/97 X |
| 4,055,086 | 10/1977 | Collins | 249/DIG. 4 |

FOREIGN PATENT DOCUMENTS

| | | | |
|---|---|---|---|
| 1250008 | 10/1971 | United Kingdom | 249/97 |
| 1274618 | 5/1972 | United Kingdom | 73/864.55 |

Primary Examiner—S. Clement Swisher
Assistant Examiner—Tom Noland
Attorney, Agent, or Firm—Fuller, House & Hohenfeldt

[57] ABSTRACT

A molten metal sampler is disclosed which includes a mold cavity defined by a steel sleeve having an accurately machined and polished interior surface and a steel disc defining one end of the sampler remote from the sample entry passage by a steel disc having a projecting bolt which becomes imbedded in the sample as it cools and in which the steel disc provides a laterally extending annular flange on the sample so that it can be suspended from a collar for a jominey test. The sleeve and integrally formed flange eliminate the need to machine the sample to prepare it for testing.

3 Claims, 4 Drawing Figures

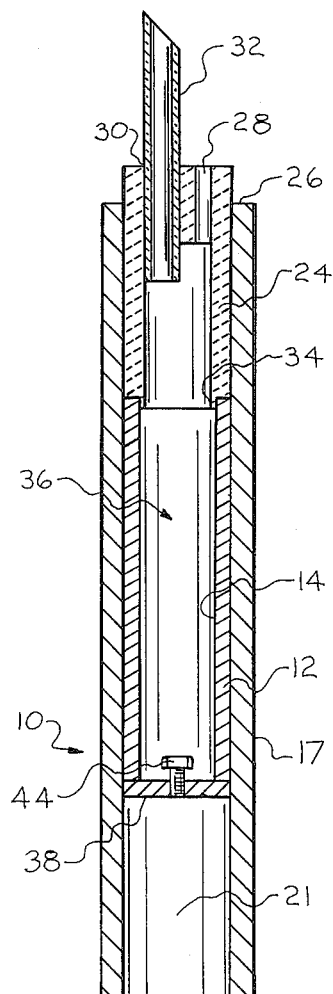
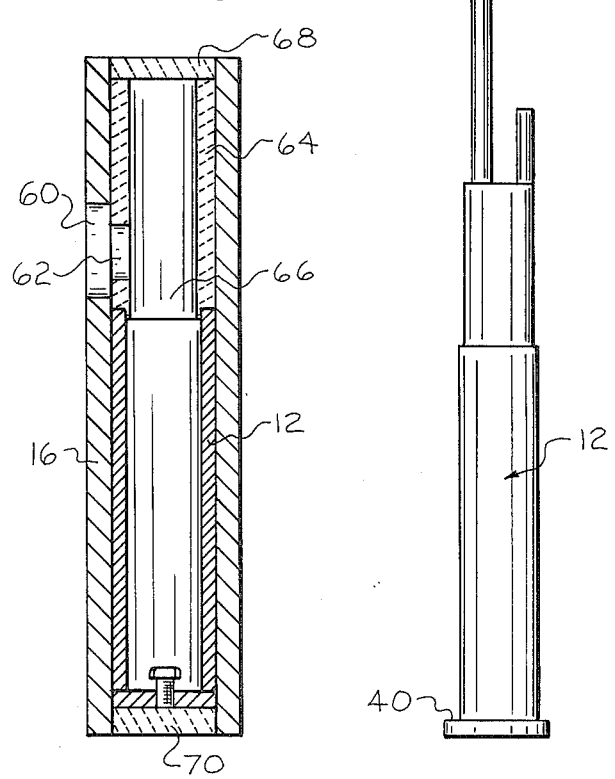
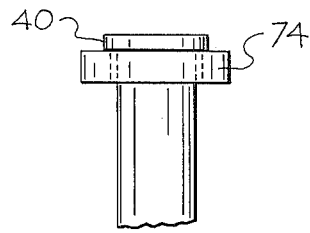

MOLTEN METAL SAMPLER FOR JOMINEY TEST

BACKGROUND OF THE INVENTION

The invention relates to molten metal sampling in which small samples are retrieved for the purpose of metallurgical analysis. In particular, the disclosure relates to a sampler for obtaining a cast sample appropriate for a jominey test. For the jominey test, a cylindrical sample is required with a flange at one end from which the sample can be suspended from the test fixture during the test procedure. The test procedure involves heating the sample to a specific temperature, dropping it in a support collar and cooling the sample with water at the lower end and measuring hardness from the quenched end toward the flanged end along flats machined on the cylindrical body. Samples which have a diameter exceeding the specified plus limit require machining, those which have a diameter less than the specified negative limit must be scrapped. The prior art jominey samplers also yielded a sample which had to be cut off at both ends to yield the proper sample length. The prior art jominey samplers employ quartz or ceramic tubes to provide a smooth surface on the exterior of the sample. However, the quartz or ceramic tubes do not hold the tolerances required to yield a sample which would fall within specified limits.

SUMMARY OF THE INVENTION

The molten metal sampler of the invention includes a steel sleeve which is accurately machined on the inside diameter to provide an accurate sample. It is also polished to provide a smooth finish on the sampler, which avoids the necessity to machine concentricity and smoothness on the exterior surface of the jominey sample to provide an accurate cylindrical surface. A molded sand sleeve provides communication between the fill passage and the steel sleeve. The molded sand sleeve facilitates shrinkage of the sample without a hanger crack, which can destroy the usefulness of the sample.

To eliminate the need to machine a peripheral shoulder on the sample as in prior art techniques, the sample cavity is provided with a steel disc at the end of the steel sleeve remote from the fill passage. The steel disc has a larger diameter than the inside diameter of the sleeve and a bolt or other anchor projecting into the mold cavity so that when the sample cools the disc is anchored to the sample to provide the required shoulder for suspension of the extending flange provided by the disc from the drop-in collar. Moreover, only one cut is required to provide the proper sample length.

A quartz fill tube for stream sampling or a side entry port or other type of technique known in the art for filling the sampler can be employed.

Further objects, advantages and features of the invention will be apparent from the disclosure.

DESCRIPTION OF THE DRAWINGS

FIG. 1 is a sectional view of one embodiment of the invention.

FIG. 2 is a diagrammatic view of a sample produced by the mold illustrated in FIG. 1.

FIG. 3 is a sectional view of a modified embodiment with a side fill port.

FIG. 4 is a fragmentary diagrammatic view of the sample suspended in a test collar.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structure. The scope of the invention is defined in the claims appended hereto.

In the drawings, FIG. 1 shows a sampler 10 which includes a steel sleeve 12 which has an inside surface 14 which is accurately machined and polished to provide a smooth interior for the exterior surface 17 of the sample 12. The steel sleeve is supported in a paperboard tube 16 which protects an exterior surface from slag or metal splash, etc. Also contained within the interior 21 of the paperboard sleeve 16 is a molded sand entry sleeve 24 which can project beyond the end 26 of the paperboard sleeve 16 and includes a vent 28 molded in place and an aperture 30 which receives a fused quartz fill tube 32. In the embodiment shown in FIG. 1, the sampler is particularly adapted for stream sampling. The molded sand sleeve 24 can have an overlapping shoulder at 34 which insures smooth entry without a discontinuity of the molten metal into the mold cavity 36. The use of the molded sand sleeve 24 in coaxial alignment with the steel sleeve 12 prevents a hanger crack from forming in the sample when it shrinks. The sand will crumble or disintegrate during shrinkage if there is any significant stress thereon to prevent a retention of part of the sample, which could cause the hanger crack.

The sample cavity 36 is defined in part by an end wall 38 which, in the disclosed construction, comprises a steel disc with a diameter larger than the inside diameter of the sleeve 12 so that there is a peripheral laterally extending flange 40 on the sample, as illustrated in FIG. 2, when the sample cools. An anchor 44, which can be in the form of a headed bolt, projects into the mold cavity 36 to anchor the disc 38 to the sample when the sample cools.

FIG. 3 discloses a modified embodiment in which the paperboard sleeve 16 has a side entry port 60 which communicates with a side entry port 62 in a molded sand sleeve 64 which is open at end 66 to enable the sample cavity to communicate with a steel sleeve 12.

The sampler shown in FIG. 3 is suitable for immersing with some type of holder. Refractory discs 68 and 70 can be employed to seal the ends of the sampler.

FIG. 4 shows the integrally formed shoulder on flange 40 supported from the collar 74 of the test fixture.

I claim:

1. A molten metal sampler for forming a smooth walled sample for later metallurgical analysis, said sampler including a smooth walled metal tube forming a mold cavity, a protective sleeve surrounding said tube, a transverse circular disc defining one end of said mold cavity positioned in abutting relationship with one end of said tube, said disc having a diameter larger than the inside diameter of said tube, said tube to provide a laterally extending flange on the sample when the sample cools and having anchor means projecting within said sleeve within said mold cavity for securing said transverse disc to the sample when the sample cools, and a fill port in said protective sleeve for introducing molten metal into said metal tube.

2. The sampler of claim 1 including a refractory sleeve at one end of and in coaxial relationship with the wall of said tube, and an entrance port for said mold cavity, said port being located in a side wall of said refractory sleeve.

3. The sampler of claim 1 including a molded sand sleeve abutting one end of said tube, and a fill passage extending longitudinally into said sand sleeve and communicating with said smooth walled tube, said sand sleeve having a shoulder overlapping said metal tube to ensure smooth entry without discontinuity of the molten metal into the metal tube.

* * * * *